United States Patent [19]

Takata et al.

[11] Patent Number: 4,849,110
[45] Date of Patent: Jul. 18, 1989

[54] METHOD AND APPARATUS FOR LIQUID CHROMATOGRAPHY

[75] Inventors: Yoshinori Takata, Chiba; Hitoshi Iwabuchi, Nakaminato, both of Japan

[73] Assignee: Hitachi, Ltd., Tokyo, Japan

[21] Appl. No.: 119,479

[22] Filed: Nov. 12, 1987

[30] Foreign Application Priority Data

Nov. 12, 1986 [JP] Japan .................. 61-267632
Apr. 3, 1987 [JP] Japan .................. 62-80971

[51] Int. Cl.⁴ ............................................. B01D 15/08
[52] U.S. Cl. .................. 210/656; 73/61.1 C; 210/198.2; 422/70; 436/161
[58] Field of Search ............ 210/659, 656, 190, 198.2, 210/635; 422/70; 73/61.1 C; 436/161

[56] References Cited

U.S. PATENT DOCUMENTS

| | | | |
|---|---|---|---|
| 3,806,321 | 4/1974 | Durrum | 422/70 |
| 3,846,074 | 11/1974 | Tulumello | 436/161 |
| 3,923,460 | 12/1975 | Parrott | 436/161 |
| 3,926,559 | 12/1975 | Stevens | 436/150 |
| 4,070,284 | 1/1978 | Fujita | 422/70 |
| 4,112,743 | 9/1978 | Mowery | 422/70 |
| 4,272,246 | 6/1981 | Fritz | 436/161 |
| 4,387,075 | 6/1983 | Morgart | 422/70 |
| 4,403,039 | 9/1983 | Ban | 210/656 |
| 4,478,713 | 10/1984 | Girot | 422/70 |
| 4,592,842 | 6/1986 | Tomlinson | 422/70 |
| 4,634,680 | 1/1987 | Kingsley | 436/161 |
| 4,654,311 | 3/1987 | Khanna | 436/175 |
| 4,715,216 | 12/1987 | Muller | 436/161 |
| 4,732,686 | 3/1988 | Small | 436/161 |

FOREIGN PATENT DOCUMENTS 55-132952 10/1980 Japan ............ 210/198.2

OTHER PUBLICATIONS

Okada, "Formation Mechanism of Dip Peaks in Nonsuppressed Ion Chromatography" Anal. Chem. 1984, p. 56.

Primary Examiner—Ernest G. Therkorn
Attorney, Agent, or Firm—Antonelli, Terry & Wands

[57] ABSTRACT

The invention relates to a liquid chromatography based on a very small liquid feeding rate, where a liquid sample containing components to be detected, such as anion species, is mixed with an eluting solution, the resulting liquid mixture is continuously passed through a separation column, whereby the components to be detected are held in the separation column, then a predetermined amount of an extraction liquid as an aliquot is injected into the stream of the liquid mixture, and the liquid mixture is continuously passed through the separation column after the injected extraction liquid has passed through the separation column. The thus obtained chromatogram has peaks corresponding to the consumptions of the components to be detected in the liquid mixture.

According to the present invention the unpractical problem that a very trace amount of a liquid sample has been so far injected when a flow rate of the eluting solution is low can be completely solved.

16 Claims, 8 Drawing Sheets 4,849,110

METHOD AND APPARATUS FOR LIQUID CHROMATOGRAPHY

BACKGROUND OF THE INVENTION

This invention relates to a method and an apparatus for liquid chromatography, and particularly to a method and an apparatus suitable for liquid chromatography where the flow rate of an eluting solution is low.

General principle of liquid chromatography is to fill an ion exchange resin or an adsorptive packing material into a separation column and feeding an eluting solution into the separation column, thereby separating components of an injected sample from one another. Examples of accurately measuring components to be detected by applying a special treatment to a sample are disclosed, for example, in Japanese- Patent Applications Kokai (Laid-open) Nos. 61-11662 and 55-132952.

With the higher speed of liquid chromatography, the feeding rate of an eluting solution has become smaller and consequently the volume of a separation column has become smaller. Thus, a volume of a sample to be introduced has also become smaller.

According to the conventional liquid chromatography, a predetermined, small amount of a sample is injected into the stream of the eluting solution and the components to be detected in the sample are separated from one another in the separation column. With the lower flow rate of the eluting solution by micro-liquid chromatography, the amount of a sample to be injected inevitably becomes a very trace amount and it is quite difficult to inject such a very trace amount of the sample into the eluting solution after the accurate volume measurement. For example, when the flow rate of an eluting solution is reduced to a few $\mu l/min.$, the amount of a sample will be in the order of nl, and it is practically difficult to accurately measure such a very trace amount of the sample.

On the other hand, the following prior art is disclosed in the field of ion chromatography, irrespectively of the reduction in the volume of a sample: Anal. Chem., 56 pp. 2073-2078 (1984), which suggests that anion species in an eluting solution are to be observed as absent peaks by continuously feeding only the eluting solution into a separation column and injecting distilled water into the stream of the eluting solution. However, the prior art suggests nothing of how to handle a liquid sample when the flow rate of the eluting solution is low.

SUMMARY OF THE INVENTION

An object of the present invention is to provide a method and an apparatus for assay on liquid chromatography, using a low flow rate of an eluting solution without accurate measurement and sampling of a very trace amount of a sample.

Another object of the present invention is to provide a method and an apparatus for quantitatively determining anion species in a sample by liquid chromatography, even if a separation column of small inner volume is used.

The present method for liquid chromatography comprises the following steps of mixing a liquid sample containing components to be detected with an eluting solution in a predetermined ratio, thereby obtaining a liquid mixture; continuously feeding the liquid mixture through a separation column, thereby equilibrating the holding states of the components to be detected in the separation column; inserting a predetermined amount of an extraction liquid as an aliquot into the stream of the liquid mixture, thereby introducing a band of the extraction liquid sandwiched by the liquid mixture at both sides into the separation column; and observing the liquid mixture effluent from the separation column after the band of the extraction liquid has passed through the separation column, thereby measuring a change in detection signals.

The present apparatus for liquid chromatography comprises a separation column filled with a filler having a holding capacity of not more than 30 $\mu eq/g$; a means for mixing a liquid sample containing components to be detected with an eluting solution; a means for continuously feeding a liquid mixture obtained by the mixing means into the separation column; a means for inserting a predetermined amount of an extraction liquid as an aliquot into the stream of the liquid mixture, the inserting means being provided upstream of the separation column; and a means for detecting peaks corresponding to the components to be detected in the effluent from the separation column.

In the present invention, a liquid mixture of the sample and the eluting solution is prepared to be acidic or neutral, and the extraction liquid is prepared to be alkaline. The anion species in a sample can be measured with a high sensitivity by using an electroconductivity detector as the detecting means.

As the alkaline extraction liquid, for example, a solution of potassium hydroxide or a solution of sodium hydroxide is suitable, and is added pulsewise to the separation column or to the stream of the liquid mixture of the eluting solution and sample.

When a sample solution is continuously fed into the separation column in advance, the components to be separated in the sample solution reach an adsorption desorption equilibrium between the column filler and the sample solution in the separation column. The column filler is an anion exchange resin of low exchange capacity and the components to be detected are anion species. Thus, an ion exchange equilibrium is established in the separation column. When a predetermined, small amount of a solution of alkali hydroxide is added thereto in the ion equilibrium state, the hydroxyl ions drive the already adsorbed anions out of the anion exchange resin to form a band region rich in the hydroxyl ions and lacking in the desired anion species on the ion exchange resin. The hydroxyl ions are developed by the desired anions in the sample and by other solute, and eluted from the separation column at the positions corresponding to the eluted sites of the anion species to be detected in the sample. The eluted hydroxyl ions combine with hydrogen ions to form water, and as a result a chromatogram lacking in the respective desired anion species is obtained.

The amounts of the desired anion species adsorbed in advance are proportional to their concentrations in a sample solution within a certain concentration range, and thus the desired anion species are quantitatively determinable. In the case of applying the present invention to measurement of cation species, a cation exchange resin is used as a column packing material, and an acidic solution such as a dilute $HNO_3$ solution is used as an extraction liquid.

How the present invention works will be described in more detail below:

As the extraction liquid, a solution completely free from the same substances as the components to be detected in the sample is used. When pure water (preferably ultra-pure water for the measurement of trace amounts of components) is used as the extraction liquid, an absent (vacant) peak of the solute of the eluting solution itself appears. When a solution containing the same substance as the solute of the eluting solution is used so as to make the same concentration in the flow passage as the extracting agent, the appearance of the peak of the solute itself can be suppressed.

In the present invention, a standard sample solution containing the same substance or substances as the component or components to be detected in the sample at a predetermined concentration as the extraction liquid can be used. In that case, a chromatogram based on the concentration difference between the sample to be detected and the standard sample can be obtained by the detector.

As the separation column, a column filled with a filler having a small adsorption, distribution or ion exchange capacity is used. For example, when a filler having an exchange capacity of 3 $\mu$eq/g is used, the necessary time from the start to feed the liquid mixture of an eluting solution and a sample into the separation column to the equilibration in the separation column is about 20 minutes. In order to attain the equilibration in the separation column within 3 hours, it is desired that a filler has an exchange capacity of not more than 30 $\mu$eq/g.

By continuously feeding the liquid mixture of an eluting solution and a sample into a separation column having a small adsorption, distribution or ion exchange capacity, the equilibration of adsorption, distribution or ion exchange can be attained. Then, by feeding a predetermined amount of an extraction liquid into the separation column for the releasing purpose, the components to be detected, which have been in an equilibrium state on the filler by adsorption, etc. under said conditions, will behave so as to maintain the equilibrium state between the components to be detected and the extraction liquid. As a result, the components to be detected, which have been held in the separation column by adsorption, etc. will be extracted into the extraction liquid and discharged from the separation column as the extraction liquid is discharged from the separation column. Through the separation column the extraction liquid moves while taking a band state as sandwiched by the liquid mixture of the eluting solution and the sample at both sides.

As the liquid mixture of the eluting solution and the sample, as continuously fed into the separation column after the insertion of the extraction liquid, moves through the separation column, the components to be detected in the sample are consumed so as to make up the sites from which the components to be detected have been released by the preceding passage of the extraction liquid, and such a band that lacks in the components to be detected moves through the separation column and is developed therein in the same manner as in the ordinary separating operation.

When the solution effluent from the separation column is monitored by a detector, a chromatogram as given in FIG. 2 can be obtained. When only one component is detected and monitored in a sample, a vacant band corresponding to the concentration of that single component can be detected as a negative peak. By properly selecting the eluting conditions, the individual components to be detected can be exhibited at positions (retention time) at which they should have been eluted in the normal liquid chromatography, as the respective negative peaks.

In the example of FIG. 2, anion components in a sample were separated in an ion exchange column and detected by an electroconductivity detector. The components to be measured according to the present invention are not limited thereto, but any of the components that can be measured by the ordinary liquid chromatography can be detected in principle by the specific separation columns and the detectors so far used in the ordinary liquid chromatography.

In the example of FIG. 2, ultra-pure water was used as the extraction liquid for the releasing purpose, but it will be comprehended from the working principle of the present invention that any other solution can be used as the extraction liquid, so far as it contains no components to be detected.

An amount of the extraction liquid to be injected into the stream of a liquid mixture of the eluting solution and the sample must be accurately measured. For the injection, an automatic injector device provided with a measuring tube and a passage switch valve is usually used, and such an injector device as an injection syringe may be used. The amount of the extraction liquid to be injected is selected according to the kind of a filler, the flow rate of an eluting solution, concentrations of components in a sample, detection sensitivity of a detector, etc. Practically, a volume that can be accurately measured by a measuring tube, etc. is set and is usually in a range of 1 $\mu$l to 1 ml.

The liquid mixture of an eluting solution and a sample is fed to the separation column at a predetermined rate, and the flow rate is not more than 2 ml/min.

In the microchromatography, a separation column having a small inner volume is used, and the inner volume of such a separation column is not more than 3 ml. The feeding volume of the liquid mixture per minute is smaller than the inner volume of the separation column.

DETAILED DESCRIPTION OF THE PREFERRED EMBODIMENTS

Figure 1:
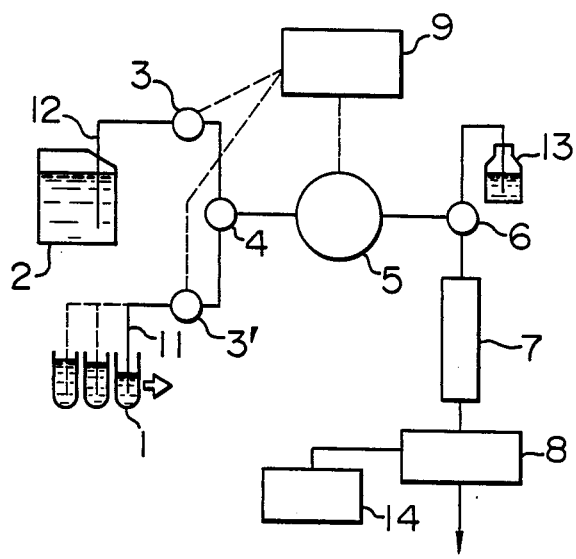
FIG. 1 is a view showing the schematic structure of an analytical apparatus according to one embodiment of the present invention.

One embodiment of the present invention will be described in detail below, referring to FIG. 1.

A plurality of sample containers 1 each containing a liquid sample containing components to be detected are provided on a turn-table, and are successively positioned at the suction site according to each assaying. The sample containers in row are intermittently moved in the arrow direction. In an eluting solution tank 2 an aqueous potassium hydrogen phthalate solution prepared to make a concentration of 0.75 mM when mixed with a sample is contained. A feed pump 5 is a reciprocal type, twin piston pump and its motion is controlled by a controller 9 so as to assure a flow rate of usually not more than 1 ml/min, particularly a micro flow rate in the order of $\mu$l/min.

A mixing device 4 is provided upstream of the feed pump 5, one of whose branches is connected to a tube 12 through an electromagnetic valve 3 and other of whose branches is connected to a suction tube 11 through another magnetic valve 3'. The suction pipe 11 is vertically moved and successively inserted into the sample containers 1 according to the intermittent movement of the sample containers 1 in row. The electromagnetic valves 3 and 3'are opened or shut by the controller 9 and the eluting solution and the liquid sample are taken into the tubes 12 and 11, respectively, in a predetermined ratio by the suction of the feed pump 5, and joined together and mixed in the mixing device 4.

The resulting liquid mixture is fed into a separation column 7 while maintaining a predetermined flow rate. In this embodiment, a mixing ratio of the eluting solution to the liquid sample is 50:50 by volume. The liquid mixture is continuously fed into the separation column 7 and discharged from the separation column 7 to the outside through a detector 8. As the detector 8, an electroconductivity monitor (type L-3700, made by Hitachi, Ltd., Japan) is used in this embodiment, but other kinds of the detectors, for example, a spectrophotometer or a coulometric monitor can be used for a desired assaying purpose.

As the separation column 7, a Hitachi packed column No. 2710SA-IC, 4 mm in inner diameter, 50 mm in length and about 2.5 ml in column inner volume, filled with Hitachi custom ion exchange resin 2710SA-IC as a filler, is used. The filler is an anion exchange resin of low exchange capacity, i.e. about 20 $\mu$eq/g. As the filler, an ion exchange resin of much smaller ion exchange capacity or an adsorbent having an adsorbing capacity in the order of $\mu$ mol/g can be also used.

An automatic feeding device 6 provided with a measuring tube is provided between the feed pump 5 and the separation column 7 and ultra-pure water contained in a solvent tank 13 is measured by the measuring tube and accurately 20 $\mu$l of the ultra-pure water can be fed into the stream of the liquid mixture of the eluting solution and the liquid sample by switching a passage switch valve provided in the automatic feeding device 6. Signals from the detector 8 are recorded in a recorder 14 as a chromatogram. The signals from the detector 8 can be also processed by a data processor to compute the concentrations of the individual components to be detected, and the computed concentrations can be displayed.

Figure 2:
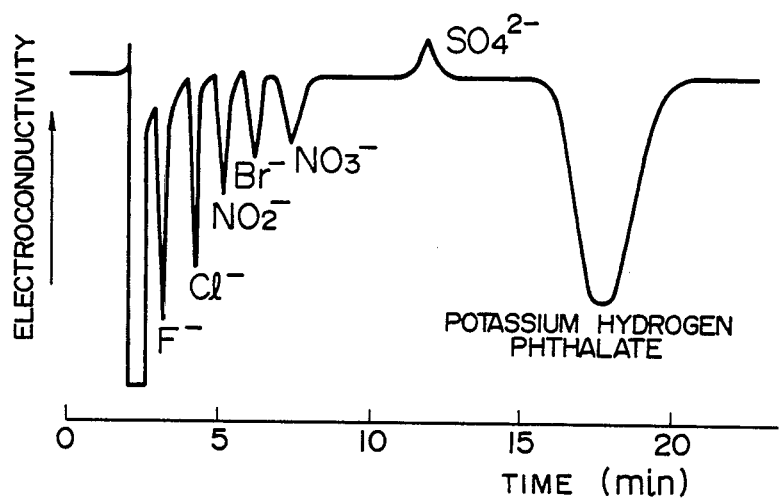
FIG. 2 is a diagram showing a measurement example obtained according to the embodiment of FIG. 1.

In the apparatus of the foregoing structure, the liquid mixture of the eluting solution and a liquid sample was fed into the separation column at a flow rate of 1 ml/min. about 2 hours after the feeding of the liquid mixture, 20 $\mu$l of pure water was injected as an extraction liquid into the stream of the liquid mixture from the automatic feeding device 6. The liquid sample contained 100 ppm each of fluoride ions ($F^-$), chloride ions ($Cl^-$), nitrite ions ($NO_2^-$), bromide ions ($Br^-$), nitrate ions ($NO_3^-$) and sulfate ions ($SO_4^{2-}$). The measurement result is shown in FIG. 2, where the peak appearing at the position of retention time of about 17 minutes after the injection of the extracting liquid is based on potassium hydrogen phthalate in the eluting solution.

In the embodiment of FIG. 1, a chromatographic assaying can be made even by continuously feeding the liquid sample without measuring its volume. Thus, in this embodiment the assaying of a liquid sample can be carried out by continuously feeding it until one assaying has been completed, without any automatically difficult procedure of measuring an amount of liquid sample in the order of ml as in the conventional micro-liquid chromatography, and the automatic assaying can be readily and effectively carried out in the present invention. Furthermore, a large number of liquid samples can be efficiently and effectively assayed by successively mixing the individual liquid samples into an eluting solution.

Figure 3:
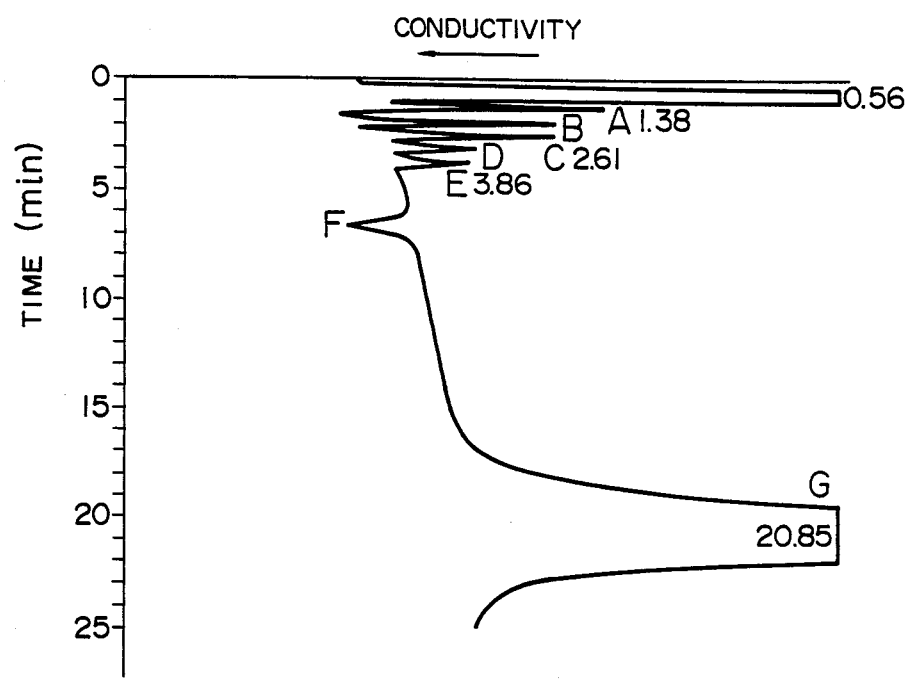
FIGS. 3 to 6 are diagrams showing test results obtained with the apparatus according to the embodiment of FIG. 1.
Figure 4:
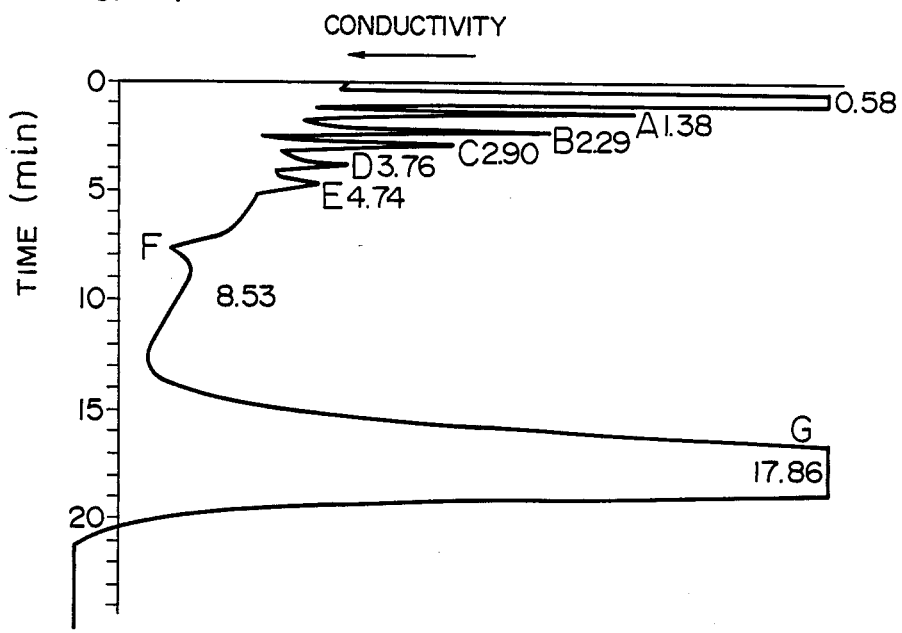
Figure 5:
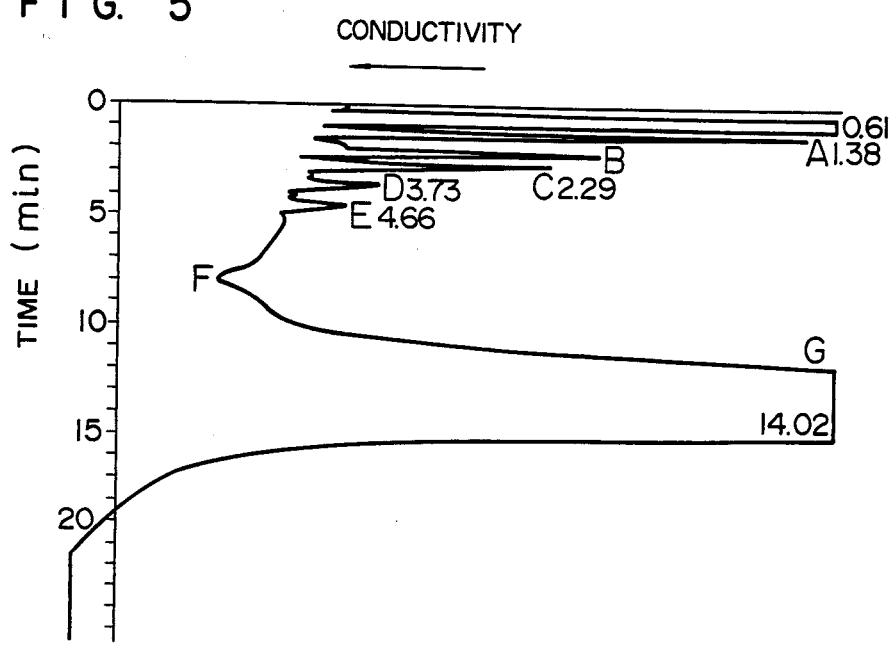
Figure 6:
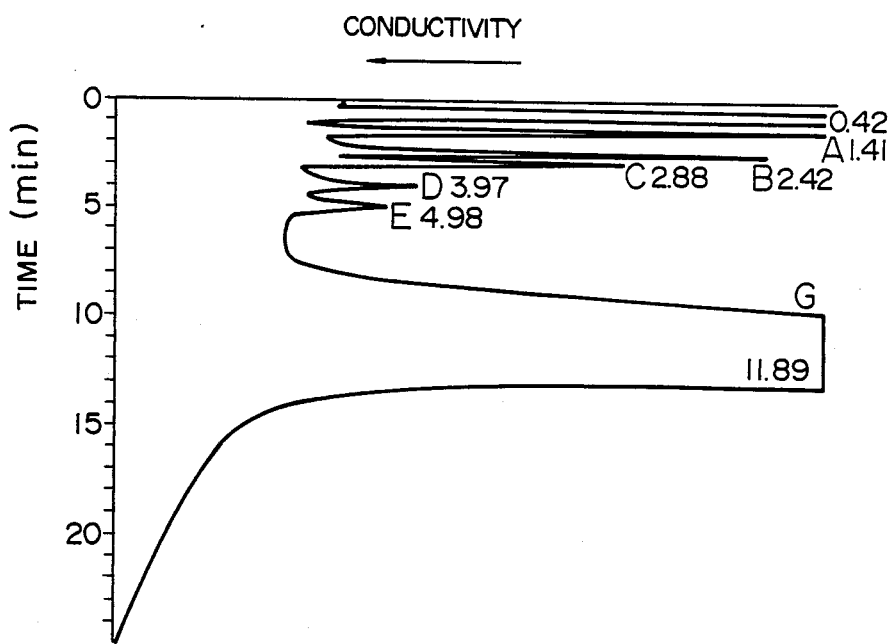

Test examples by changing the pH of an eluting solution in the apparatus of FIG. 1 are shown in FIGS. 3 to 6, where the feed rate by the fed pump 5 was 1.0 ml/min., the liquid sample was an aqueous solution containing 1 ppm each of $F^-$, $Cl^-$, $NO_2$, $Br^-$, $NO_3^-$ and $SO_4^{2-}$, and the separation column 7 was maintained at 40° C. FIG. 3 shows the test at pH 4.5, FIG. 4 shows that at pH 4.3, FIG. 5 shows that at pH 4.1 and FIG. 6 shows that at pH 4.0. Individual peaks A, B, C, D, E and F correspond to said ion species in the order of description. The test results reveal that the individual component peaks have a longer retention time with decreasing pH, whereas the peak G of the solute of the eluting solution has a shorter retention time with decreasing pH.

Figure 7:
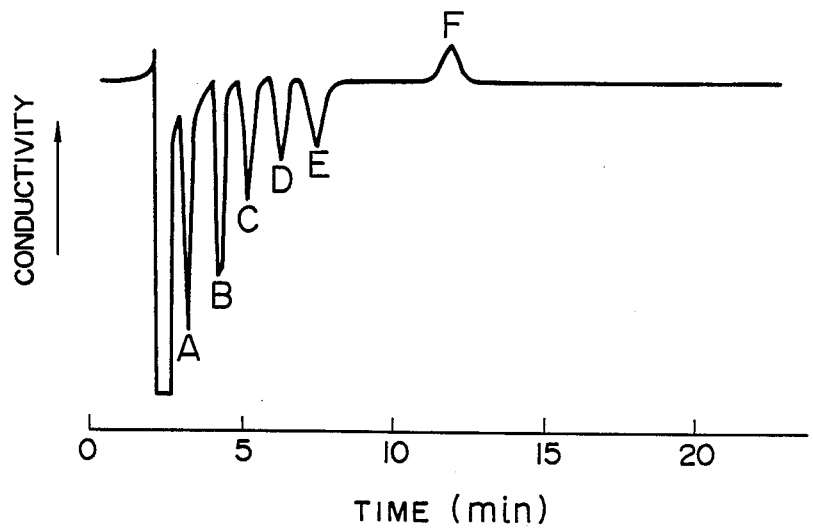
FIG. 7 is a diagram showing a measurement example obtained according to a further embodiment of the present invention.

A further embodiment of the present invention is that a solution of potassium hydrogen phthalate is used as the extraction liquid in the solvent tank 13 of the embodiment of FIG. 1 for the releasing purpose. The extraction liquid for the releasing purpose is prepared so as to have the same concentration and the same pH as those of potassium hydrogen phthalate of the eluting solution in the flow passage in the analytical apparatus, while other assaying conditions are identical with those of FIG. 2. The result is shown in FIG. 7. The peak F of $SO_4^{2-}$ appears on the positive side from the base line as in the embodiment of FIG. 2. As is comprehensible from FIG. 7, the appearance of the disturbing peak due to the solute of the eluting solution can be suppressed according to this embodiment.

Another embodiment of the present invention will be described below, referring to FIG. 8, which shows a schematic flow structure of a chromatographic apparatus according to the present invention.

An eluting solution 31 and a liquid sample 32 are controlled in their flow rates by high speed electromagnetic valves 33 and 33' and mixed in a predetermined ratio at a mixing device 4, and fed into a separation column 7 through an injector device 35 by a feed pump 5. A predetermined amount of an alkaline solution is injected at the injector device 35 by a microsyringe 36. A detector 8 is an electroconductivity monitor having a cell 8'. The electroconductivity cell 8' and the separation column 7 are placed in a column oven 10 and kept constantly at 40° C. The electroconductivity monitor 8 is connected to a data processor 37 to record the retention time, peak height, peak area, etc.

As the separation column, a column filled with a filler of small adsorption, distribution or ion exchange capacity is used. For example, when a filler having an exchange capacity of 3 μeq/g is used, the necessary time from the start to feed the liquid mixture of the eluting solution and the liquid sample to the equilibration in the separation column is about 20 minutes. In order to attain the equilibration in the separation column within 3 hours, it is necessary to use a filler having a holding capacity of not more than 30 μeq/g. In this embodiment, the same ion exchange resin as in the embodiment of FIG. 1 is filled in the separation column.

Figure 8:
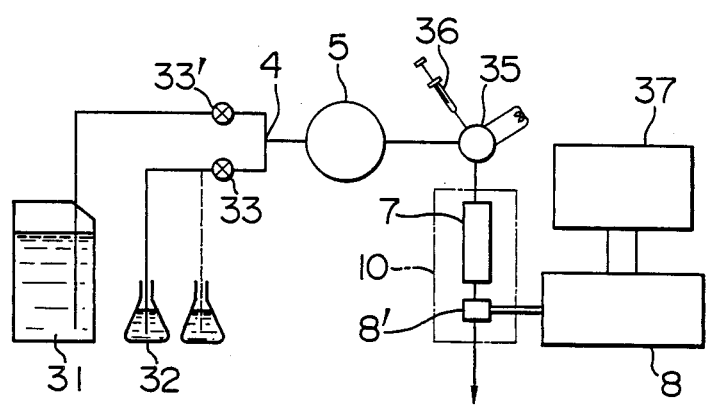
FIG. 8 is a view showing the schematic structure of an analytical apparatus according to another embodiment of the present invention.
Figure 9:
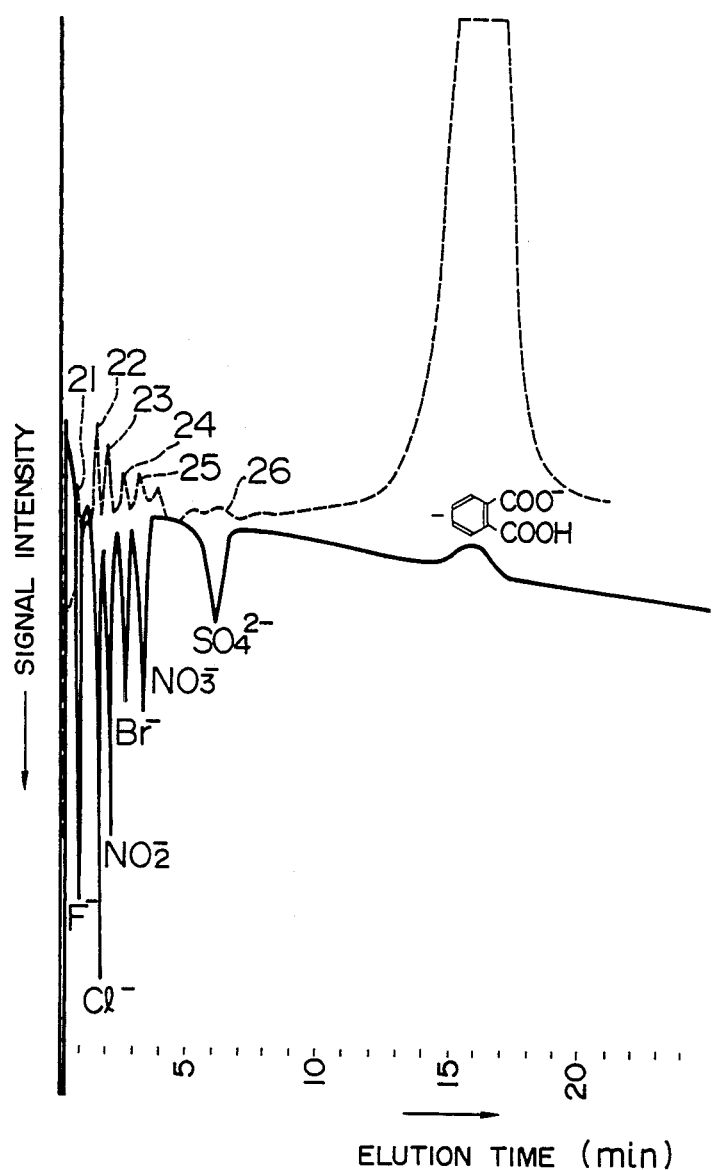
FIG. 9 is a diagram comparing an ion chromatogram with a vacant chromatogram.
Figure 10:
FIGS. 10 to 13 are comparative diagrams of vacant chromatogram, using various extraction liquids.
Figure 11:
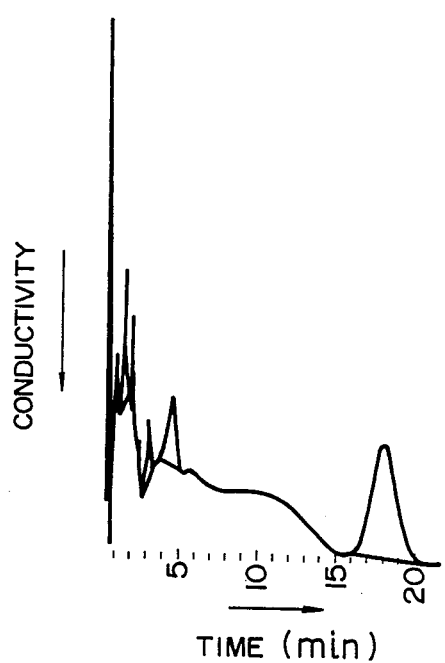
Figure 12:
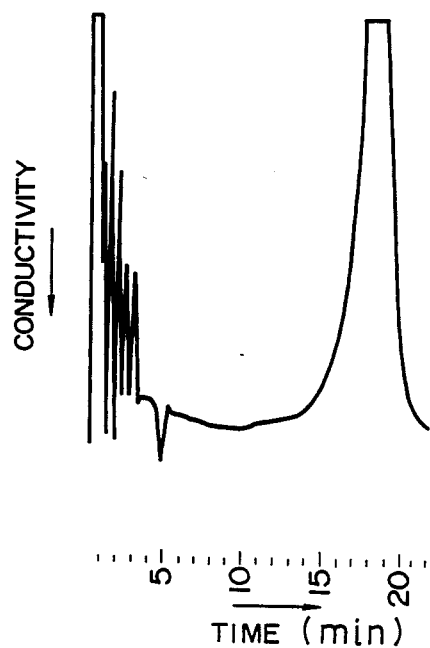
Figure 13:
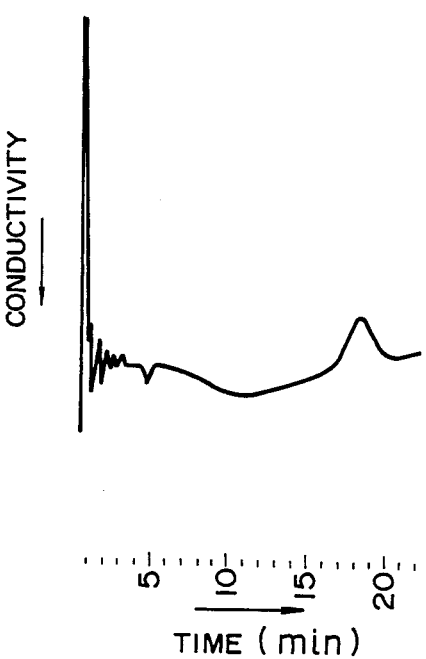

Chromatogram of FIG. 9 shows a test example using the apparatus of FIG. 8, where the eluting solution was 1.5 mM potassium hydrogen phthalate (pH 4.3) and the liquid sample was an aqueous solution containing 4.0 ppm each of $F^-$, $Cl^-$, $NO_2^-$, $Br^-$, $NO_3^-$ and $SO_4^-$. By opening or closing the electromagnetic valves 33 and 33', the eluting solution and the liquid sample were mixed in a ratio of 50:50 by volume and 250 μl of pure water (dotted line) or 1 μl of a solution containing 100 ppm each of said ion species (full line) was added to the liquid mixture at the injector device 35. The effluate was monitored by way of the output from the electroconductivity monitor 8. In FIG. 9, the upward direction shows a decreasing electroconductivity. That is, the full line shows the ordinary ion chromatogram, whereas the dotted line shows "a vacant chromatogram" lacking in the desired ion species.

In FIG. 9, the peaks of dotted line are vacant anion peals such as $F^-$ by 21, $Cl^-$ by 22, $NO_2^-$ by 23, $Br^-$ by 24, $NO_3^-$ by 25 and $SO_4^-$ by 26. It can be seen in the vacant chromatogram that peaks lacking in the components appear at the sites where the components are to be eluted by ion chromatography and there are disturbances after the peak of $NO_3^-$ or before and after the peak of $SO_4^{-2}$ when pure water is injected into the stream of the liquid mixture. A vacant peak of phthalate ions appears 16 minutes after the injection of pure water as the extraction liquid.

FIGS. 10 to 13 shows the states of vacant chromatogram by injecting various extraction liquids. The liquid sample containing 4.0 ppm each of the same anion species as in FIG. 9 was used. In FIGS. 10 to 13, a predetermined amount of one of various extraction liquids was injected into the stream of the liquid mixture at the injector device 35 of FIG. 8. That is, 25 μl of 1 mM potassium hydroxide was injected in FIG. 10, 25 μl of 0.75 mM potassium hydrogen phthalate was injected in FIG. 11, 250 μl of pure water was injected in FIG. 12, and 25 μl of pure water was injected in FIG. 13 to obtain the vacant chromatograms. When 1 mM potassium hydroxide was injected as in FIG. 10, a good chromatogram with less disturbance of base line was obtained. When the chromatogram of FIG. 10 was compared with that of injecting 25 μl of pure water of FIG. 13, the chromatogram of FIG. 10 had an about 3-fold higher sensitivity.

Figure 14:
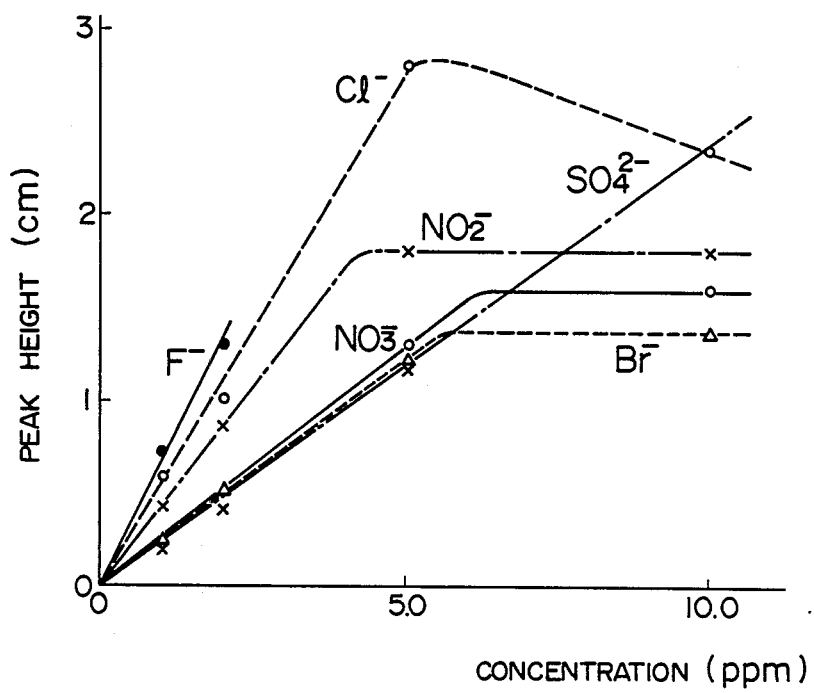
FIG. 14 is a diagram showing calibration curves of various anion species according to the present invention.

FIG. 14 shows calibration curves obtained by changing the concentrations of the anion species in the liquid sample 32 between 1 and 10 ppm and injecting 25 μl of 1 mM potassium hydroxide into the stream of the liquid mixture. It is apparent from FIG. 14 that by the injection of potassium hydroxide, the respective anion species show a good linearity in certain concentration ranges.

As the extraction liquid to be injected, any alkaline solution can be used, so long as it can be dissociated to give hydroxyl ions, and lithium hydroxide, sodium hydroxide, potassium hydroxide, ammonium hydroxide, etc. can be practically used as a solute in the alkaline solution.

According to the embodiment of FIG. 8, "a vacant chromatogram" with less disturbance of base line can be obtained, and thus anion species can be quantitatively determined by continuously feeding a liquid sample in a certain concentration range to the separation column.

What is claimed is:
1. A method for liquid chromatography, which comprises:
   (i) mixing a liquid sample containing components to be detected with an eluting solution in a predetermined ratio, thereby obtaining a liquid mixture;
   (ii) continuously feeding the liquid mixture at a low flow rate through a separation column, thereby equilibrating the holding states of the components to be detected in the separation column;
   (iii) inserting a predetermined amount of an extraction liquid as an aliquot into the stream of the liquid mixture, thereby introducing a band of the extraction liquid sandwiched by the liquid mixture at both sides into the separation column;
   (iv) observing the liquid mixture effluent from the separation column after the band of the extraction liquid has passed through the separation column, thereby measuring a change in detection signals; and
   (v) detecting components contained in said liquid sample based upon the change in detection signals.

2. A method according to claim 1, wherein the separation column is filled with a filler having a holding capacity of not more than 30 μeq/g.

3. A method according to claim 1, wherein the extraction liquid is a solution free from the components to be detected but containing the same substance as the solute of the eluting solution.

4. A method according to claim 1, wherein the liquid mixture is fed at a predetermined flow velocity and at a smaller feeding volume per minute than the inner volume of the separation column.

5. A method according to claim 1, wherein the extraction liquid is a known sample solution.

6. A process according to claim 1, wherein the detecting of ion species is performed by detecting, as negative peaks, vacant bands corresponding to the components to be detected.

7. A process according to claim 1, wherein the liquid mixture is acidic or neutral, and the extraction liquid is alkaline.

8. A process according to claim 7, wherein the alkaline extraction liquid is an alkaline solution selected from the group consisting of lithium hydroxide, sodium hydroxide, potassium hydroxide and ammonium hydroxide.

9. A process according to claim 7, wherein the components to be detected are anions, and the separation column has anion exchange resin incorporated therein.

10. A process according to claim 1, wherein the extraction liquid is inserted in a pulsewise manner.

11. A process according to claim 1, wherein the components to be detected are cations, the separation column has cation exchange resin incorporated therein, and the extraction liquid is an acidic solution.

12. A process according to claim 1, wherein the liquid mixture is continuously fed through the separation column at a flow rate of not more than 2 ml/min.

13. A process according to claim 1, wherein the inner volume of the separation column is not more than 3 ml.

14. A method for liquid chromatography, which comprises:
(i) mixing a liquid sample containing ion species to be detected with an eluting solution in a predetermined ratio, thereby obtaining an acidic liquid mixture;
(ii) continuously feeding the liquid mixture at a flow rate through a separation column;
(iii) inserting a predetermined amount of an alkaline extraction solution as an aliquot into the stream of the liquid mixture, thereby introducing a band of the extraction liquid sandwiched by the liquid mixture at both sides into the separation column;
(iv) observing the liquid mixture effluent from the separation column after the band of the extraction liquid has passed through the separation column, thereby measuring a change in detection signals; and
(v) detecting ion species in the liquid sample based upon the change in detection signals.

15. A method according to claim 14, wherein the alkaline extraction solution is a solution of caustic alkali.

16. A method according to claim 14, wherein the eluting solution is a solution of potassium hydrogen phthalate.

* * * * *